United States Patent [19]

Peers-Trevarton

[11] Patent Number: 4,784,141

[45] Date of Patent: Nov. 15, 1988

[54] LEAD LOCKING MECHANISM FOR CARDIAC PACERS

[75] Inventor: Charles A. Peers-Trevarton, Pompano Beach, Fla.

[73] Assignee: Cordis Leads, Inc., Miami, Fla.

[21] Appl. No.: 81,354

[22] Filed: Aug. 4, 1987

[51] Int. Cl.⁴ .............................................. A61N 1/00
[52] U.S. Cl. ............................. 128/419 P; 439/784; 439/805
[58] Field of Search ...................... 128/419 P, 419 PS; 439/784, 805

[56] References Cited

U.S. PATENT DOCUMENTS

| | | | |
|---|---|---|---|
| 902,235 | 10/1908 | Kellner | 439/805 |
| 1,710,416 | 4/1929 | Goeller | 439/805 |
| 3,010,747 | 11/1961 | Bondon | 439/805 |
| 3,183,476 | 5/1965 | Sacks et al. | 439/805 |
| 3,649,367 | 3/1972 | Purdy | 128/419 PS |
| 3,760,332 | 9/1973 | Berkovits et al. | 128/419 P |
| 3,824,556 | 7/1974 | Berkovits et al. | 128/419 P |
| 4,278,093 | 7/1981 | Lafortune et al. | 128/419 P |
| 4,672,979 | 6/1987 | Pohndorf | 128/419 P |

FOREIGN PATENT DOCUMENTS 622571 5/1949 United Kingdom ............... 439/805

Primary Examiner—Francis Jaworski
Assistant Examiner—George Manuel
Attorney, Agent, or Firm—Lockwood, Alex, Fitzgibbon & Cummings

[57] ABSTRACT

A lead locking mechanism suitable for use in a cardiac pacer is provided for axial in-line lead attachment in a pacer neck thereby permitting reduction in pacer neck thickness. The lead locking mechanism includes a substantially fixed annular collar and a hollow screw member threadedly mounted within the annular collar. The annular collar and hollow screw member confine a radially contractable and expandable lead locking member therebetween which functions to clamp a lead connector pin in response to movement of the hollow screw member.

6 Claims, 2 Drawing Sheets

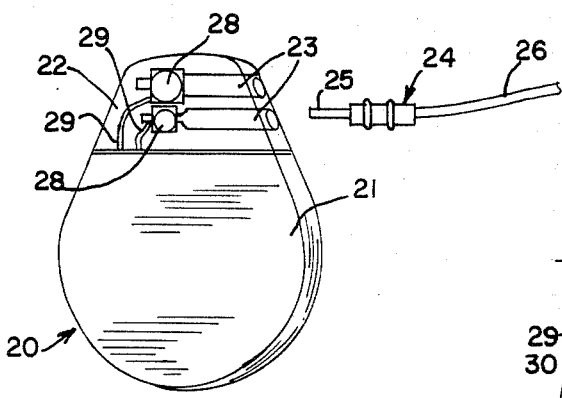
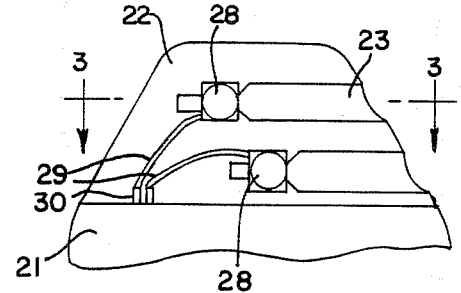
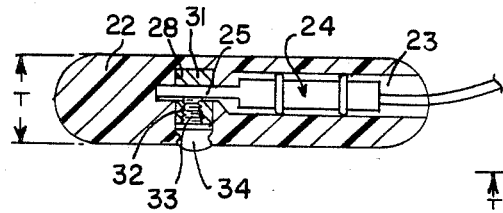
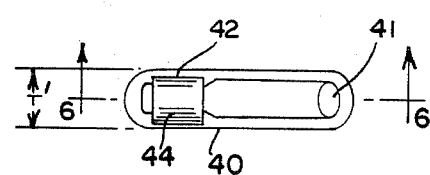
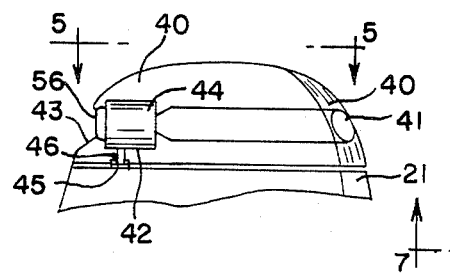
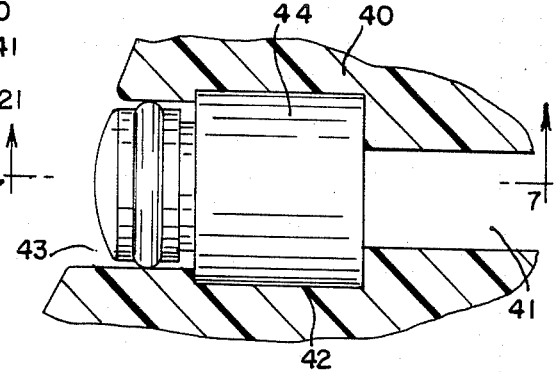

4,784,141

LEAD LOCKING MECHANISM FOR CARDIAC PACERS

BACKGROUND OF THE INVENTION

The present invention is directed to a new and improved cardiac pacer lead locking mechanism, more particularly to a lead locking mechanism which is designed for mounting in a pacer neck aperture to receive and electrically connect the terminal pin of a lead connector to the electronic circuit of the pacer. More specifically, the invention is directed to a lead locking mechanism which includes a plurality of relatively movable parts, two of which are axially aligned and another of which is confined between the first two, relative axial movement of the first two parts causing operation of the confined part for the clamping of a terminal pin of a lead connector.

Conventionally, a cardiac pacer or pacemaker includes a case or can which contains a power supply in the form of a battery as well as the necessary electronic circuitry. The case further includes a neck or housing which is designed to accept a pair of lead terminals which are connected to an electrode placed in contact with or adjacent to the cardiac muscle being stimulated. The neck or housing includes a pair of spaced apertures or passageways, each of which receives a terminal pin and each of which includes some form of lead locking mechanism for clamping the pins to the pacer so as to establish electrical continuity.

Continuing efforts are being made to reduce the size of cardiac pacers or their components, bearing in mind that pacers are intended to be implanted. One area of importance with respect to size reduction is the neck portion of a pacer, and that is the area to which the present invention is directed.

It has been conventional to utilize a lead locking mechanism in association with each pacer neck aperture, which lead locking mechanism is oriented transversely or radially with respect to the aperture and to the terminal pin to be clamped. Among the components used in such a locking mechanism is a clamping set screw which radially or transversely engages the longitudinal axis of the terminal pin and which is mounted within and accessible through an aperture communicating with a side surface of the pacer neck in order to permit application of a tool for adjustment of the set screw. A separate, frictionally held seal is inserted in the outermost end portion of the set screw aperture to prevent body fluid intrusion during the implanted condition of the pacer. The transverse relationship of these types of conventional lead locking mechanisms adds to the thickness of the pacer neck as dictated by the length of the set screw, screw block and frictionally held seal. Additionally, the frictionally held seal presents a potential problem by raising the possibility of its becoming loose from or popping out of the aperture in which it is inserted. In other words, the seal is not always as positively held as might be desired.

The present invention permits substantial reduction in the thickness of the neck portion of a cardiac pacer and also provides positive clamping of a seal in the lead terminal aperture of the neck to prevent body fluid intrusion. Reduction in pacer neck thickness is accomplished by axial or longitudinal alignment of the various parts of the lead locking mechanism in the pacer neck aperture. This improved lead locking mechanism consists basically of interacting component parts plus a seal, the components being in the form of annular members, two of which are threadedly advanceable and retractable relative to one another in coaxial alignment, and another of which is confined between the first two parts to be acted upon to radially contract or expand in clamping or releasing the terminal pin of a lead connector. The mechanism further functions to hold the seal within the pacer neck aperture in a positive manner even while the lead locking mechanism itself is being adjusted to clamp or release a terminal pin, thereby not only effectively and continuously sealing the pacer neck aperture but also preventing the popping out of the seal during and following implantation of the pacer.

All of the foregoing is generally accomplished within the confines of the pacer neck aperture itself. Typically included is the presence of only a slight enlargement of a relatively short portion of the pacer neck aperture. A chamber is formed in which the lead locking mechanism is positioned. This slight enlargement is oriented in an axial or longitudinal direction relative to the aperture, thereby permitting a substantial reduction in the thickness of the pacer neck. Such reduction typically approaches 50 percent, for example, reducing the width of a conventional pacer neck from 10 mm. to approximately 5 or 6 mm.

It will be seen that the subject invention provides a number of substantial advantages over existing lead locking mechanism designs and pacer neck configurations. Reduction of pacer neck thickness is, of course, an important advantage as described above. An additional advantage resides in the in-line operation of the lead locking mechanism and simultaneous insertion and holding of the terminal pin, these two functions being accomplished coaxially and in axially opposed directions thereby adding to the efficiency of assembly during implantation of the cardiac pacer. Still a further advantage, as referred to above, is the controlled holding and positioning of the seal at all times during clamping of the lead, thus eliminating any additional necessary step to seal the neck aperture. Simplicity of design constitutes an important advantage. Still further, an efficient and positive electrical connection is obtained and maintained. The lack of design complexity provides long life advantages. Other advantages will become apparent from the following description of preferred embodiment of the invention.

SUMMARY OF THE INVENTION

A lead locking mechanism for use in a cardiac pacer includes first and second coaxially and relatively advanceable and retractable members confining therebetween a third member which is radially contractable and expandable in response to relative axial movement of the first and second members. The mechanism is mounted coaxially in a pacer neck aperture in a substantially longitudinal orientation and includes a captive seal which at all times is in sealing engagement with the interior surface of the aperture, even during operational adjustment of the lead locking mechanism.

BRIEF DESCRIPTION OF THE DRAWINGS

The especially important features of the present invention are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a generally perspective view in partly fragmented form illustrating a conventional implantable dual lead cardiac pacer and a cardiac pacing lead;

FIG. 2 is an enlarged fragmentary elevational view of the neck portion of a conventional dual lead cardiac pacer utilizing a prior art form of lead locking mechanism;

FIG. 3 is a sectional view of the pacer neck taken along line 3—3 of FIG. 2;

FIG. 4 is a fragmentary, generally perspective view of the neck portion of a cardiac pacer incorporating the lead locking mechanism of the present invention;

FIG. 5 is a top plan view of the neck portion taken along line 5—5 of FIG. 4;

FIG. 6 is an enlarged fragmentary partial sectional view of the neck portion as viewed along line 6—6 of FIG. 5;

DESCRIPTION OF THE PREFERRED EMBODIMENT

Figure 7:
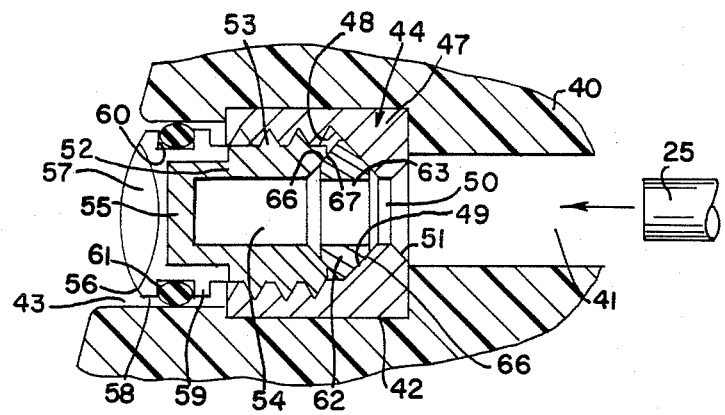
FIG. 7 is an enlarged fragmentary section of the lead locking mechanism of the present invention as viewed along line 7—7 of FIG. 6.

FIGS. 1 through 3 illustrate an implantable cardiac pacer 20 of conventional design including a case or can 21 made from titanium or other suitable material, the case containing conventional electronic circuitry and power supply means arranged in the conventional manner. The pacer 20 includes a neck 22 which will at times be referred to hereinafter as a housing and which is typically fabricated from molded epoxy resin. The neck or housing 22 is provided with an aperture or longitudinally extending passageway 23 which opens outwardly of one end of the neck and extends for a length that terminates before the opposite end of the neck. The pacer illustrated is a dual lead pacer requiring a pair of lead terminals 24 (only one of which is shown in FIG. 1) and a pair of the apertures or passageways 23 (both of which are shown in FIG. 1). Each lead 24 is provided with a terminal pin 25 and forms a part of a lead assembly including an electrode 26 which is in contact with or placed adjacent to a cardiac muscle in a generally known manner.

The closed end of each passageway 23 has mounted therein in a direction that extends transversely or radially of each such longitudinal passageway 23 a conventional form of lead locking mechanism 28, which is connected with a conductor wire 29 connected to a feed-through 30 (FIG. 2) which in turn is connected to the electronic circuitry and power supply (not shown) contained within case 21. Basically, terminals 24 are inserted in apertures 23 with terminal pins 25 suitably locked in place by lead locking mechanisms 28 as best illustrated in FIG. 3.

Each lead locking mechanism includes a set screw block 31 provided with a threaded aperture 32 receiving a threaded set screw 33 therein. In use, set screw 33 is retracted sufficiently to permit block 31 to receive pin 25 of a lead connector 24 therethrough, the pin being clamped in circuit closing relation by advancing set screw 33 transversely against pin 25. In order to prevent intrusion of body fluids into neck 22, a sealing plug 34 of a silicone elastomer is inserted in the aperture receiving the lead locking mechanism outwardly of set screw 33 and is held therein by friction.

Ongoing objectives in the packaging of implantable stimulators include reduction in length, width and thickness. Reduction in length and width of the implantable stimulator is achieved by the use of integrated and hybrid circuits as well as reduction in the size of the power source. Although some reduction in thickness may be attained as circuits and power sources of reduced size become available, currently the limiting factor in thickness reduction is the use of the transverse set screw type of lead locking mechanism shown in FIGS. 1 through 3 in a dual lead pacer. This rather conventional mechanism including block 31, set screw 33 and elastomer sealing plug 34 materially limits thickness reduction in a dual lead pacer because each lead locking mechanism must be partially incorporated on its side surface. A perpendicular relationship exists, thereby governing the thickness "T" of the neck of the pacer as shown in FIG. 3. This relationship constitutes a constraint on reducing the thickness of the neck.

Because of the conventional nature of the lead locking mechanism of the type shown in FIGS. 1 through 3, complete details have not been provided. FIGS. 4 through 10 illustrate in detail the preferred lead locking mechanism of the present invention. Referring to FIG. 4, the same type of pacer case 21 can be utilized, with the improved lead locking mechanism forming a part of a thinner neck or housing 40 of the present invention. Referring specifically to improved neck 40, same is provided with a longitudinally extending annular passageway or aperture 41 adapted to receive a lead connector 24 provided with terminal pin 25 of the type previously described. The lead connector is insertable in aperture 41 from the right as viewed in FIGS. 4 and 5, the opposite end of aperture 41 communicating with chamber 42 which in turn communicates with an annular end opening 43 extending through the opposite end of the neck 40. The improved lead locking mechanism 44 is anchored in chamber 42 adjacent open end 43 of aperture 41.

While the lead connector aperture extends throughout the longitudinal width of neck 40, such aperture and the lead locking mechanism associated therewith are in axial alignment, thus eliminating the radial or perpendicular relationship described in FIGS. 1 through 3 and thus permitting substantial reduction in thickness of the neck from thickness T of FIG. 3 to thickness T' of FIG. 5. It has been found that this alignment which is achieved by utilizing the lead locking mechanism of the present invention permits a reduction in pacer neck thickness from the conventional thickness of approximately 10 mm to a materially reduced thickness of approximately 5 to 6 mm. Thus, it can be seen that a reduction in thickness approaching 50 percent is attainable.

As shown in FIG. 4, each lead locking mechanism 44 is in electrical continuity with the feed-through 45 via a conductor wire 46 welded or otherwise bonded to lead locking mechanism 44 and to the feed-through 45. Feed-through 45 is in electrical continuity with the electronic circuitry and power supply (neither being shown) that are contained with case 21.

FIG. 7 illustrates the basic components of the improved lead locking mechanism 44. A housing or annular collar 47 is suitably mounted within chamber 42 by press-fitting or other acceptable means, so as to be fixed within chamber 42 and generally coaxially oriented relative to aperture 41. Housing 47 can be considered as functioning as a fixed nut of somewhat extended axial length by reason of being provided with an internal threaded area 48 extending from one end thereof but terminating short of the opposite end thereof. The opposite end of housing 47 is provided with an internally projecting ramp or chamfer surface 49 which terminates in an annular flat portion 50 which in turn merges with a frusto-conical end surface area 51. Housing 47 is preferably fabricated of stainless steel, such as 304 stainless steel.

A second member of the lead locking mechanism is in the form of a hollow screw 52 which also may preferably be formed from 304 stainless steel. Hollow screw 52 along the outer surface thereof is provided with a threaded area 53 which is in threaded engagement with threaded area 48 of housing 47. Screw 52 has a hollow interior which is in the form of an annular core 54 having a diameter which closely approximates the diameter of flat portion 50 of housing 47 and is in substantial axial alignment therewith. The outer end of screw 52 is closed to provide an end wall or terminus 55 for the interior core 54. Bonded to the outer surface of the outer end portion of screw 52 is a cap 56 which may be fabricated of non-conductive material, such as polyethersulfone, polycarbonate or other similar material. Cap 56 is provided along its outer radial surface with a slot 57 adapted to receive a suitable tool in the nature of a screwdriver for advancement and retraction of screw 52 relative to and within the housing 47.

An annular portion of cap 56 outwardly of housing 47 and adjacent end wall 55 of screw 52 is provided with a pair of axially spaced, outwardly projecting ridges 58 and 59 which define therebetween an annular groove 60. Held captive within the groove 60 but projecting radially outwardly therefrom is a continuous seal in the form of an O-ring 61 with the outer surface thereof in engagement with the annular surface of the end opening 43 of aperture 41. In this manner a continuous seal is maintained between the lead locking mechanism and the outer end of aperture 41 at all times including those times when screw 52 is advanced or retracted for lead locking or unlocking purposes.

Figure 8:
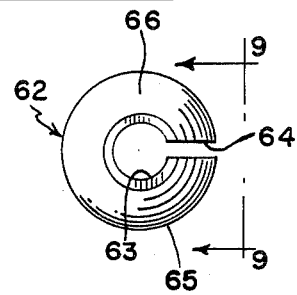
FIG. 8 is an elevational end view of a preferred radially acting member of the lead locking mechanism of the present invention.
Figure 9:
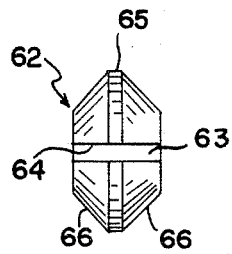
FIG. 9 is a side elevational view of the radially acting member of FIG. 8 as viewed along line 9—9 of FIG. 8.

The lead locking mechanism is completed by the provision of a contractable and expandable locking ring 62 which is confined between housing 47 and screw 52. As best shown in FIGS. 8 and 9, compression ring 62 is provided with a central annular core 63 which is dimensioned to be of an initial circumferential size that is no smaller than the core 54 of screw 52 and the ring portion 50 of housing 47 (FIG. 7) prior to lead clamping. Central annular core 63 is also substantially coaxial with the core 54 and the ring portion 50. Ring 62 has an axially extending circumferential split to define a slot 64 of sufficient width to permit inner core 63 of the ring 62 to be compressed to a smaller diameter in a manner to be described. The outer surface area of ring 62 is formed centrally thereof with an annular flat band 65 which merges in opposite axial directions with a pair of oppositely facing frusto-conical ramp portions of chamfers 66.

Ring 62 is confined between housing 47 and screw 52. One ramp portion 66 of ring 62 is in engagement with ramp portion 49 of housing 47 while the opposite ramp portion 66 of ring 62 is in engagement with a frusto-conical ramp of chamfer 67 formed along the inner surface of the innermost end of screw 52. In this manner, ring 62 is confined between oppositely directed frusto-conical ramp surfaces 49 and 67 with these surfaces being in engagement with paralleling ramp surfaces 66 of ring 62. Ring 62 may also be formed from 304 stainless steel.

Figure 10:
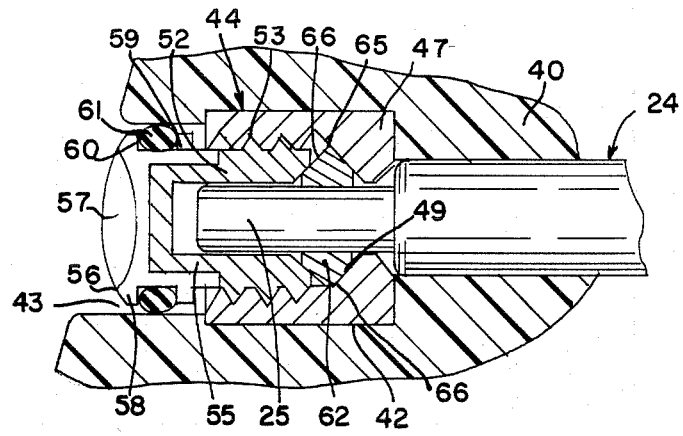
FIG. 10 is an enlarged fragmentary section of the lead locking mechanism of the present invention illustrating the clamping of a lead terminal pin therein.

FIG. 7 illustrates the lead locking mechanism of the present invention in condition to receive the terminal pin 25 of a terminal connector. Pin 25 is advanced axially along passageway 41 of neck 40, through the core portion defined by flat surface 50 of housing 47, through core 63 of compression ring 62 and into internal core 54 of screw 52 to obtain the final position illustrated in FIG. 10. Upon adequate insertion of pin 25, screw 52 is suitably advanced by a screwdriver or the like axially within housing 47. Ramp portion 49 of housing 47 is fixed by reason of housing 47 being fixed in chamber 42. Ramp portion 67 of screw 52 advances against parallel ramp portion 66 of compression ring 62. Accordingly, the application of applied pressure and holding pressure against the oppositely inclined ramp portions 66 of ring 62 causes ring 62 to compress to the extent permitted by the width of slot 64 formed radially therein. The resulting compression causes ring 62 to circumferentially compress in order to engage and clamp terminal pin 25 as illustrated in FIG. 10.

With this arrangement, a lead connector 24 is locked by the mechanism 44 within passageway 41 and is placed in circuit closing relationship with the circuitry and battery carried by pacer case 21. Retraction of screw 52 causes relaxation of pressure on the outer peripheral ramps 66 of ring 62, thereby permitting expansion of ring 62 as a result of the inherent resiliency of the material from which the ring is formed, and thereby releasing terminal pin 25 to permit withdrawal of the lead connector 24 from the passageway 41 of neck 40.

Although only one lead locking mechanism of the present invention is illustrated and described in connection with FIGS. 4 through 10, it will be understood that dual mechanisms may form a part of a pacer neck while retaining the thickness reduction advantages. In a dual-chambered cardiac pacemaker, a plurality of such locking mechanisms, each associated with its respective pacer neck aperture, may be incorporated without compromising the significant reduction in thickness of a cardiac pacer neck that is made possible according to this invention. The coaxial alignment of the cooperating parts of the lead locking mechanism described permits improvement in sealing the neck passageway from intrusion of body fluids. Seal 61 is held captive at all times and is continuously functioning as an effective seal during operation of the lead locking mechanism. There is no possibility of the seal popping out of its cavity, nor is there any significant threat of the seal becoming loose and ineffective. The internal core surface 63 of compression ring 62 has a sufficient axial area to establish and maintain a highly efficient electrical contact with terminal pin 25. All of the parts described may be economically formed and, due to the relative simplicity of the design, such parts are capable of long life.

While a particular embodiment of the invention has been shown and described, it will be obvious to those skilled in the art that changes and modifications may be made therein without departing from the invention in its broader aspects; and, therefore, the aim in the appended claims is to cover all such changes and modifications as fall within the true spirit and scope of the invention.

I claim:

1. A lead locking mechanism for use within a longitudinal aperture through a neck portion of a cardiac pacer, said lead locking mechanism clamping a lead connector to close an electrical circuit, said lead locking mechanism comprising:
   a substantially fixed annular collar mounted within the longitudinal aperture, said annular collar having an opening sized and shaped to closely slidably receive the lead connector, said annular collar having a threaded axially directed internal surface, said annular collar further including an internal frusto-conical chamfer surface that is defined between said axially-directed internal surface and said opening of the annular collar;
   a hollow screw member threadedly mounted within said threaded axially directed internal surface of the annular collar, said hollow screw member having an annular core sized and shaped to closely receive the lead connector, said hollow screw member having a frusto-conical end surface; and
   a lead connector locking ring confined between said internal frusto-conical chamfer surface of the annular collar and said frusto-conical end surface of the hollow screw member, said lead locking ring having a pair of generally oppositely facing frusto-conical ramp portions that extend between respective end faces of the locking ring and a circumferential portion of the locking ring that is between said respective end faces and that extends beyond said end faces of the locking ring, said locking ring further including a hollow central annular core and an axially directed slot which is a circumferential split of the locking ring that contracts into secure ring-like engagement of the lead connector when said hollow screw member is threadedly moved into said substantially fixed annular collar.

2. The lead locking mechanism of claim 1, wherein said hollow screw member has an externally oriented end face that is a closed end, and said closed end includes a screw head having tool engaging means for threadedly advancing and retracting said hollow screw member.

3. The lead locking mechanism of claim 2, wherein said closed end of the hollow screw member has an annular portion radially spaced from the longitudinal aperture through the neck portion of the cardiac pacer, said annular portion has an annular retention groove, and a sealing ring is in said annular retention groove and engages and seals the longitudinal aperture through the neck portion of the cardiac pacer.

4. In a cardiac pacer provided with a case and a neck portion secured onto the case, the neck portion having a longitudinal aperture therethrough, and a lead locking mechanism clamping a lead connector to close an electrical circuit, the improvement of a lead locking mechanism comprising:
   a substantially fixed annular collar mounted within the longitudinal aperture, said annular collar having an opening sized and shaped to closely slidably receive the lead connector, said annular collar having a threaded axially directed internal surface, said annular collar further including an internal frusto-conical chamber surface that is defined between said axially-directed internal surface and said opening of the annular collar;
   a hollow screw member threadedly mounted within said threaded axially directed internal surface of the annular collar, said hollow screw member having an annular core sized and shaped to closely receive the lead connector, said hollow screw member having a frusto-conical end surface; and
   a lead connector locking ring confined between said internal frusto-conical chamfer surface of the annular collar and said frusto-conical end surface of the hollow screw member, said lead locking ring having a pair of generally oppositely facing frusto-conical ramp portions that extend between respective end faces of the locking ring and a circumferential portion of the locking ring that is between said respective end faces and that extends beyond said end faces of the locking ring, said locking ring further including a hollow central annular core and an axially directed slot which is a circumferential split of the locking ring that contracts into secure ring-like engagement of the lead connector when said hollow screw member is threadedly moved into said substantially fixed annular collar.

5. The cardiac pacer according to claim 4, wherein said hollow screw member has an externally oriented end face that is a closed end, and said closed end includes a screw head having tool engaging means for threadedly advancing and retracting said hollow screw member.

6. The cardiac pacer according to claim 5, wherein said closed end of the hollow screw member has an annular portion radially spaced from the longitudinal aperture through the neck portion of the cardiac pacer, said annular portion has an annular retention groove, and a sealing ring is in said annular retention groove and engages and seals the longitudinal aperture through the neck portion of the cardiac pacer.

* * * * *

UNITED STATES PATENT AND TRADEMARK OFFICE
CERTIFICATE OF CORRECTION

PATENT NO. : 4,784,141
DATED : November 15, 1988
INVENTOR(S) : Charles A. Peers-Trevarton It is certified that error appears in the above-identified patent and that said Letters Patent is hereby corrected as shown below:

```
Col. 2, line 45, insert --a-- after "of".
Col. 8, line 15, "chamber" should read --chamfer--.
```

Signed and Sealed this

Twenty-second Day of August, 1989

Attest:

DONALD J. QUIGG

*Attesting Officer*  *Commissioner of Patents and Trademarks*